US00PP15635P2

(12) United States Plant Patent
Pierce

(10) Patent No.: US PP15,635 P2
(45) Date of Patent: Mar. 8, 2005

(54) ***ANTIRRHINUM* PLANT NAMED 'SULTE BROE'**

(50) Latin Name: *Antirrhinum×hybrida*
Varietal Denomination: Sulte Broe

(75) Inventor: Robert Pierce, Watsonville, CA (US)

(73) Assignee: Goldsmith Seeds, INC, Gilroy, CA (US)

( * ) Notice: Subject to any disclaimer, the term of this patent is extended or adjusted under 35 U.S.C. 154(b) by 37 days.

(21) Appl. No.: 10/818,353

(22) Filed: Apr. 5, 2004

(51) Int. Cl.[7] ..... A01H 5/00
(52) U.S. Cl. ..... Plt./322
(58) Field of Search ..... Plt./322

*Primary Examiner*—Kent Bell
(74) *Attorney, Agent, or Firm*—C. A. Whealy

(57) ABSTRACT

A new and distinct cultivar of *Antirrhinum* plant named 'Sulte Broe', characterized by its outwardly spreading, decumbent and mounded plant habit; freely branching habit; freely flowering habit; and numerous flowers that are orange in color.

1 Drawing Sheet

Botanical classification/cultivar designation: *Antirrhinum×hybrida* cultivar Sulte Broe.

BACKGROUND OF THE INVENTION

The present Invention relates to a new and distinct cultivar of *Antirrhinum* plant, commercially known as a trailing Snapdragon, botanically known as *Antirrhinum hybrida*, and hereinafter referred to by the cultivar name Sulte Broe.

The new *Antirrhinum* is a product of a planned breeding program conducted by the Inventor in Gilroy, Calif. The objective of the breeding program is to create new early and freely flowering *Antirrhinums* with trailing and mounded plant habit and attractive leaf and flower coloration.

The new *Antirrhinum* originated from a cross-pollination made by the Inventor in September, 2000 of a proprietary selection of *Antirrhinum hybrida* identified as code number 24-1, not patented, as the female, or seed parent, with a proprietary selection of *Antirrhinum hybrida* identified as code number 42-1, not patented, as the male, or pollen parent. The new *Antirrhinum* was selected as a single plant from the resulting progeny of the cross-pollination in a controlled environment in Gilroy, Calif. in May, 2001.

Asexual reproduction of the new cultivar by terminal vegetative cuttings since May, 2001, in Gilroy, Calif. has shown that the unique features of this new *Antirrhinum* are stable and reproduced true to type in successive generations.

SUMMARY OF THE INVENTION

Plants of the cultivar Sulte Broe have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sulte Broe'. These characteristics in combination distinguish 'Sulte Broe' as a new and distinct cultivar:

1. Outwardly spreading, decumbent and mounded plant habit.
2. Freely branching habit.
3. Freely flowering habit.
4. Numerous flowers that are orange in color.

In side-by-side comparisons conducted in Gilroy, Calif., plants of the new *Antirrhinum* differed from plants of the female parent selection in the following characteristics:

1. Plants of the new *Antirrhinum* were more upright than plants of the female parent selection.
2. Plants of the new *Antirrhinum* flowered earlier than plants of the female parent selection.
3. Plants of the new *Antirrhinum* and the female parent selection differed in flower color as plants of the female parent selection had red-colored flowers.

In side-by-side comparisons conducted in Gilroy, Calif., plants of the new *Antirrhinum* differed from plants of the male parent selection in the following characteristics:

1. Plants of the new *Antirrhinum* were more freely branching than plants of the male parent selection.
2. Leaves of plants of the new *Antirrhinum* were smaller than leaves of plants of the male parent selection.
3. Pants of the new *Antirrhinum* flowered earlier than plants of the male parent selection.

Plants of the new *Antirrhinum* differ from plants of the cultivar Sulte Reeda, disclosed in U.S. Plant patent application Ser. No. 10/818,363, primarily in flower color.

Plants of the new *Antirrhinum* can be compared to plants of the cultivar Luminaire Orange and Yellow, not patented. In side-by-side comparisons conducted in Gilroy, Calif., plants of the new *Antirrhinum* differed from plants of the cultivar Luminaire Orange and Yellow in the following characteristics:

1. Plants of the new *Antirrhinum* were more upright than plants of the cultivar Luminaire Orange and Yellow.
2. Leaves of plants of the new *Antirrhinum* were narrower than leaves of plants of the cultivar Luminaire Orange and Yellow.
3. Flowers of plants of the new *Antirrhinum* were darker orange in color than flowers of plants of the cultivar Luminaire Orange and Yellow.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Antirrhinum.*

The photograph at the top of the sheet comprises a side perspective view of a typical plant of 'Sulte Broe' grown in a container.

The photograph at the bottom of the sheet is a close-up view of typical flowers and leaves of 'Sulte Broe'.

DETAILED BOTANICAL DESCRIPTION

Plants of the cultivar Sulte Broe have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures ranging from 24 to 29° C., night temperatures ranging from 13 to 18° C. and light levels about 2,000 foot-candles. Plants used for the photographs and description were about 12 weeks from planting rooted cuttings. In the following description, color references are made to The Royal Horticultural Society Colour Chart, 1995 Edition, except where general terms of ordinary dictionary significance are used.

Botanical classification: *Antirrhinum hybrida* cultivar Sulte Broe.

Parentage:

*Female parent.*—Proprietary selection of *Antirrhinum hybrida* identified as code number 24-1, not patented.

*Male parent.*—Proprietary selection of *Antirrhinum hybrida* identified as code number 42-1, not patented.

Propagation:

*Type cutting.*—Terminal vegetative cuttings.

*Time to initiate roots, summer and winter.*—About 12 to 16 days at 21 to 23° C.

*Time to develop roots, summer and winter.*—About 25 to 30 days at 21 to 23° C.

*Root description.*—Fine, fibrous; white in color.

*Rooting habit.*—Freely branching.

Plant Description:

*Form.*—Annual flowering plant; initially upright, then low trailing and outwardly spreading; decumbent; uniformly mounded plant form. Freely branching habit; about nine basal branches per plant. Pinching enhances development of lateral branches.

*Usage.*—Appropriate for hanging baskets, window boxes, patio containers and landscape applications.

*Plant height.*—About 14 cm.

*Plant diameter* (*area of spread*).—About 41 cm.

*Vigor.*—Moderately vigorous to vigorous; moderate to rapid growth rate.

*Lateral branches.*—Length: About 27 cm. Diameter: About 2 mm. Internode length: About 2.25 cm. Texture: Smooth. Color: 147C.

*Foliage description.*—Arrangement: Opposite before flowering; alternate after flowers develop; simple. Length: About 4 cm. Width: About 1.4 cm. Shape: Elliptic. Apex: Broadly acute. Base: Attenuate. Margin: Entire. Texture, upper and lower surfaces: Pubescent. Venation pattern: Pinnate, arcuate. Color: Developing and fully expanded leaves, upper surface: 147A. Developing and fully expanded leaves, lower surface: 147B. Venation, upper and lower surfaces: 147B. Petiole length: About 1 cm. Petiole diameter: About 1 mm. Petiole color, upper and lower surfaces: 146C.

Flower description:

*Flower type and habit.*—Single bi-labiate flowers arranged on terminal racemes; flowers opposite. Freely flowering habit, usually about six to seven open flowers and about nine flower buds per raceme. Flowers face outwardly. Flowers not persistent. Flowers not fragrant.

*Natural flowering season.*—Long flowering period, spring until autumn; flowering continuous during this period. Plants start flowering about eight weeks after planting rooted cuttings.

*Flower longevity.*—Flowers last about one week on the plant.

*Flower length.*—About 2.5 cm.

*Flower width.*—About 1.6 cm.

*Flower depth.*—About 3.5 cm.

*Flower buds.*—Length: About 9 mm. Diameter: About 6 mm. Shape: Ovoid. Color: 10C.

*Corolla.*—Shape/arrangement: Broadly tubular; five modified petals; upper two and lower three petals fused. Petal lobe apices: Rounded. Petal lobe margin: Entire. Length, upper petal lobes: About 2.3 cm. Length, lower petal lobes: About 1.2 cm. Width, upper petal lobes: About 1.4 cm. Width, lower petal lobes: About 1 cm. Texture, upper and lower surfaces of petal lobes: Smooth; velvety. Texture, throat: Pubescent. Color: When opening, upper petal lobes, upper surface: 4B; towards the throat, 4D. When opening, lower petal lobes, upper surface: 4B; palate, 3A. When opening, all petal lobes and tube, lower surface: 186C. Fully opened, upper petal lobes, upper surface: 169A to 169B. Fully opened, lower petal lobes, upper surface: 169A to 169B; palate, 15A. Fully opened, all petal lobes and tube, lower surface: 186C.

*Sepals.*—Quantity/arrangement: Three to five per flower; fused at base. Length: About 8 mm. Width: About 4 mm. Shape: Elliptic. Apex: Acute. Margin: Entire. Texture, upper and lower surfaces: Densely pubescent. Color, upper surface: 147C. Color, lower surface: 147B.

*Pedicels.*—Length: About 4 mm. Diameter: About 1 mm. Strength: Strong; flexible. Angle: About 45° from the stem. Color: 147C.

*Reproductive organs.*—Androecium: Stamen quantity: Four per flower. Anther size: About 2 mm by 3 mm. Anther shape: Oval, bi-lobed. Anther color: 13B. Pollen amount: Moderate. Pollen color: 13B. Gynoecium: Pistil quantity: One per flower. Pistil length: About 1.5 cm. Style length: About 1.3 cm. Style color: 145D. Stigma color: 145B. Ovary color: 145B.

*Seeds/fruit.*—Seed and fruit development has not been observed.

Disease/pest resistance: Plants of the new *Antirrhinum* have not been observed to be resistant to pathogens and pests common to *Antirrhinum.*

It is claimed:

1. A new and distinct cultivar of *Antirrhinum* plant named 'Sulte Broe', as illustrated and described.

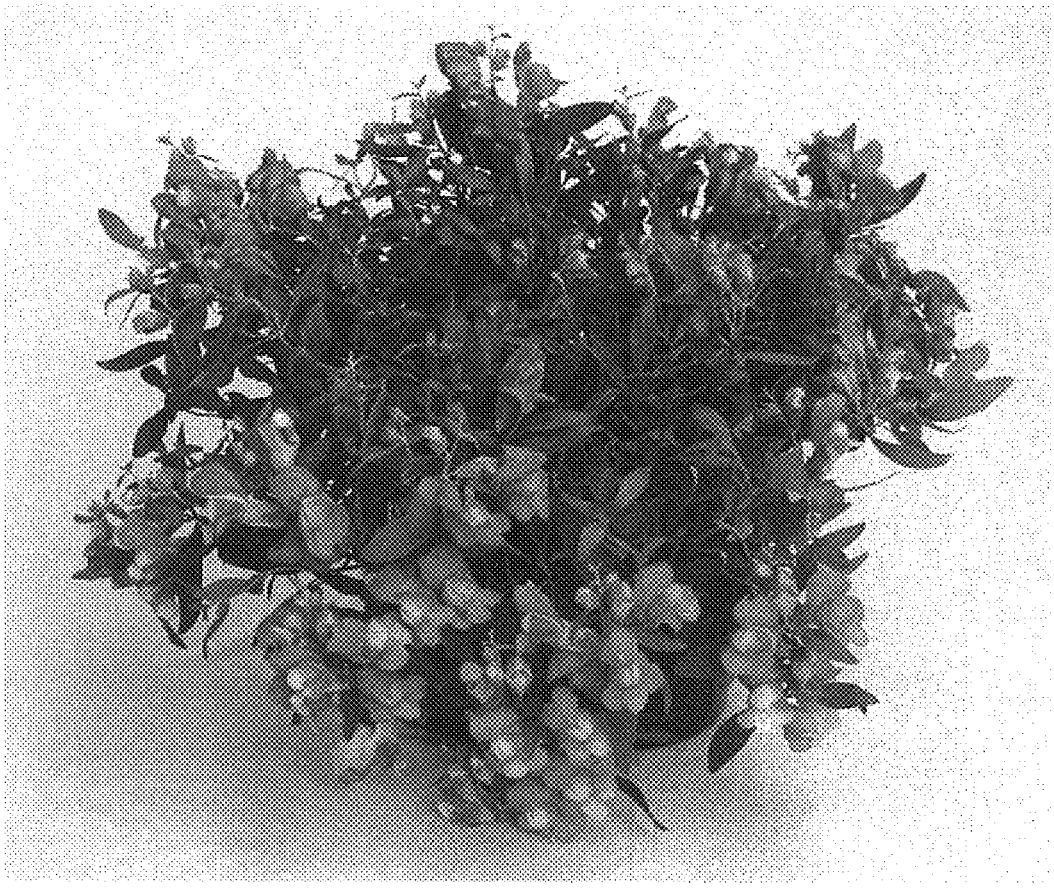
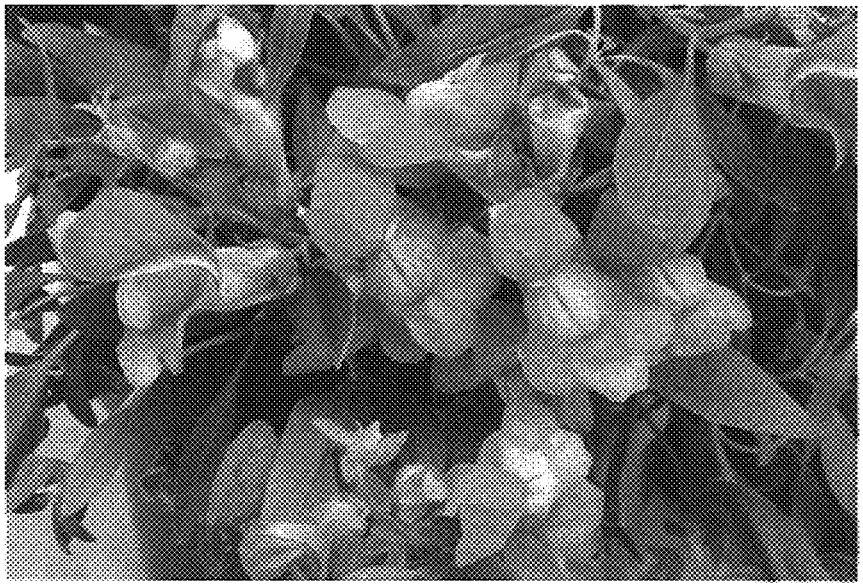

* * * * *